(12) United States Patent
Fama

(10) Patent No.: US 9,849,028 B2
(45) Date of Patent: Dec. 26, 2017

(54) CONTACT LENS APPLICATOR

(71) Applicant: Antonio Fama, Orlando, FL (US)

(72) Inventor: Antonio Fama, Orlando, FL (US)

( * ) Notice: Subject to any disclaimer, the term of this patent is extended or adjusted under 35 U.S.C. 154(b) by 0 days.

(21) Appl. No.: 14/884,541

(22) Filed: Oct. 15, 2015

(65) Prior Publication Data

US 2017/0105872 A1 Apr. 20, 2017

(51) Int. Cl.
A61F 9/00 (2006.01)

(52) U.S. Cl.
CPC .................. A61F 9/0061 (2013.01)

(58) Field of Classification Search
CPC ..................................... A61F 9/0061
USPC ........................... 294/1.2; D16/331; 206/5.1
See application file for complete search history.

(56) References Cited

U.S. PATENT DOCUMENTS

| | | | | |
|---|---|---|---|---|
| 3,424,486 A * | 1/1969 | Corley | ................ | A61F 9/0061 294/1.2 |
| 3,879,076 A * | 4/1975 | Barnett | ................ | A61F 9/0061 294/1.2 |
| 4,071,272 A * | 1/1978 | Drdlik | ................ | A61F 9/0061 294/1.2 |
| 4,123,098 A * | 10/1978 | Shoup | ................ | A61F 9/0061 294/1.2 |
| 4,126,345 A * | 11/1978 | List | ................ | A61F 9/0061 294/1.2 |
| 4,332,408 A * | 6/1982 | Cointment | ............ | A61F 9/0061 294/1.2 |
| 4,750,771 A * | 6/1988 | Emmett | ................ | A61F 9/0061 15/104.001 |
| D323,517 S * | 1/1992 | Hoeft | ............ | D16/331 |
| 5,456,508 A * | 10/1995 | Kozar | ................ | A61F 9/0061 294/1.2 |
| 5,941,583 A * | 8/1999 | Raimondi | ............ | A61F 9/0061 206/5.1 |
| 6,398,277 B1 * | 6/2002 | McDonald | ............ | A61F 9/0061 294/1.2 |
| 6,494,021 B1 * | 12/2002 | Schlagel | ............ | B29D 11/0024 294/1.2 |
| 6,955,432 B2 * | 10/2005 | Graham | ................ | A61F 9/0061 294/1.2 |
| 9,296,160 B2 * | 3/2016 | Clements | ........... | B29D 11/0023 |

* cited by examiner

Primary Examiner — Paul T Chin
(74) Attorney, Agent, or Firm — Michael W. Starkweather

(57) ABSTRACT

A contact lens applicator for use in the application and removal of contact lenses, is disclosed. The contact lens applicator comprises a hollow cylindrical tube defining a curved portion at one end having a straight portion attached to a suction bulb at the distal end. The end tip surface of the curved portion defines a generally solid concave-shaped cup surface having a center hole surrounded by an outer edge circular ring of smaller diameter holes for allowing air to pass in and out of the cylindrical tube through the cup surface. The diameter of the cylindrical tube and cup surface are slightly greater than the diameter of a contact lens. In use, the contact lens applicator temporarily grasps using air pressure a soft contact lens for applying the soft contact lens to a user's eye and for removing a soft contact lens therefrom without discomfort to the user or damage to the lens.

1 Claim, 1 Drawing Sheet

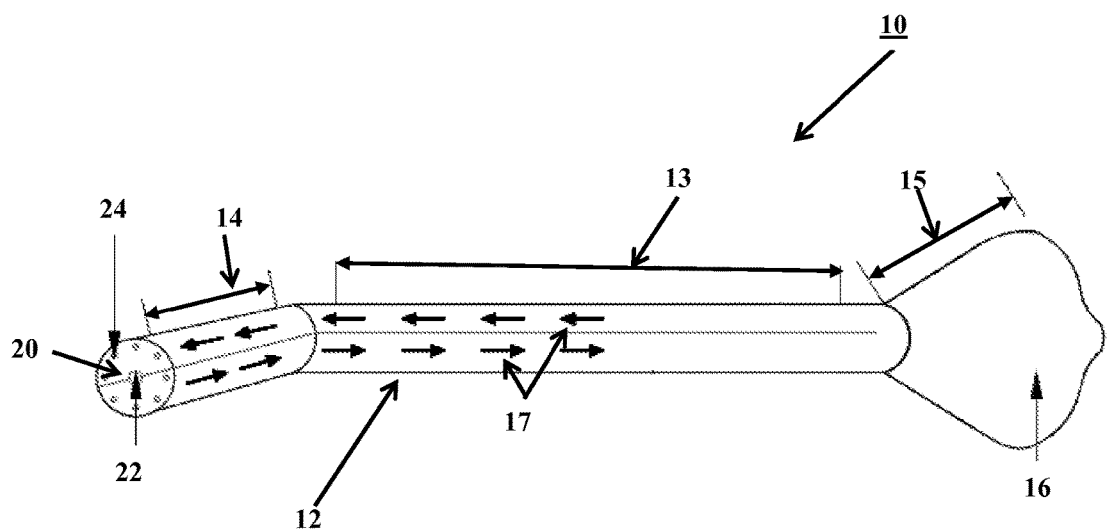

CONTACT LENS APPLICATOR

FIELD OF THE INVENTION

This invention relates generally to improvements in contact lens applicators, and more particularly to an applicator for applying a soft contact lens to the surface of the human eye.

BACKGROUND OF THE INVENTION

Contact lenses are usually applied to the eye and removed therefrom manually by the user. For application of a contact lens, the lens is placed concave side upward on a finger of the user and placed onto the cornea. For removal of the lens from the eye, the user grasps the lens at its edges using his thumb and forefinger to lift the lens off of the cornea. In the case of a soft contact lens, the user manually buckles the lens by pinching the grasped edges to lift the lens off the cornea. Many persons, however, experience considerable difficulty in placing and removing contact lenses, especially persons having limited manual dexterity and post-operative cataract patients who have minimal vision in the absence of the crystalline lens of the eye.

The prevailing method employed in placing a contact lens on the eye is for the user to wet the end of one finger, usually the index finger, with an appropriate fluid and place the lens on the wet finger which is then moved toward the eye to carry the lens into contact therewith. Simultaneously, the other hand is usually employed to hold the eyelids, making the manipulation of the lens in the vicinity of the eye a very clumsy operation. This method is neither easy nor accurate, and presents serious danger of damaging the cornea since the eye cannot focus on the lens or the finger as the finger is brought close to the eye. Thus, the final step of actually placing the lens on the cornea in the proper position is guesswork to a substantial degree.

Also, individuals required to use contact lenses must regularly perform the task of placing a contact lens into each eye. The most common method of inserting a contact lens involves bathing the contact lens in a saline or other sterile lubricating solution, placing the contact lens on a fingertip and placing the lens onto the eye with the supporting finger. To do this the finger is placed under the contact lens to support the contact lens and the face of the individual is tilted downwards. At the same time, the eyelids of the eye receiving the lens are held open and the contact lens is lifted into the eye.

Prior art contact lens applicators are generally known. The early applicators were designed primarily for the application of rigid contact lenses. Such known devices have included holders, suction apparatus, spring-loaded devices, lighting devices and eyepieces. Additionally, there have been structures which are specifically designed for soft lens application and removal.

The prior art devices may be described generally as comprising manipulation means for establishing a suction between the lens and the applicator means for holding the lens in a desired position during application or removal. Such devices, however, have involved suction created means, moving parts and other relatively complex expensive components. Further, such devices are relatively difficult to use by less dexterous individuals, for example the typical post-cataract patient who ordinarily is a person of advanced age. Known devices require the full use of one and often both hands of the user, thus making difficult or impossible manipulation of the user's eyelid or eyelids, if necessary.

Therefore, there is a need for a software contact lens applicator that allows both hands to be free for manipulation of upper and lower eyelids if necessary.

SUMMARY

A contact lens applicator for use in the application and removal of contact lenses, is disclosed. The contact lens applicator comprises a hollow cylindrical tube defining a curved portion at one end attached to a suction bulb at the distal end. The end tip surface of the curved portion defines a generally solid concave-shaped cup surface having a center hole surrounded by an outer edge circular ring of smaller diameter holes for allowing air to pass in and out of the cylindrical tube through the cup surface. The diameter of the cylindrical tube and cup surface are slightly greater than the diameter of a contact lens. In use, the contact lens applicator temporarily grasps using air pressure a soft contact lens for applying the soft contact lens to a user's eye and for removing a soft contact lens therefrom without discomfort to the user or damage to the lens.

It is a basic objective of the present invention to provide a contact lens applicator for use in the application and removal of contact lenses as to avoid or minimize obscuring of vision and to be most conveniently suited to the particular positioning required in the accurate placement and removal of contact lenses.

Another objective of the present invention is to provide a contact lens applicator designed to avoid hurt or damage to the eye or to a contact lens during the placement and removal process.

BRIEF DESCRIPTION OF THE DRAWINGS

To further clarify various aspects of some example embodiments of the present invention, a more particular description of the invention will be rendered by reference to specific embodiments thereof which are illustrated in the appended drawing. It is appreciated that the drawing depicts only illustrated embodiments of the invention and are therefore not to be considered limiting of its scope. The invention will be described and explained with additional specificity and detail through the use of the accompanying drawing in which:

FIG. 1 is a perspective view of the contact lens applicator of the present invention.

DETAILED DESCRIPTION OF THE INVENTION

Referring now to FIG. 1, there is shown a contact lens applicator 10 for use in the application and removal of contact lenses. The contact lens applicator 10 comprises a hollow cylindrical tube 12 defining a curved portion 14 at one end attached to a suction bulb 16 at the opposite or distal end. The end tip surface 20 of curved portion 14 defines a generally solid concave-shaped cup surface 20 having a center hole 22 surrounded by an outer edge circular ring of smaller diameter holes 24 for allowing air to pass in and out of the cylindrical tube 12 through cup surface 20, as will be more fully described below. The diameter of the cylindrical tube 12 and cup surface 20 are slightly greater than the diameter of a contact lens (not shown), more specifically fifty millimeters or less.

In use for applying a contact lens, a person using their fingers slightly squeezes the suction bulb 16 and places the cup surface 20 gently over the convex side of a contact lens (not shown). Next, when the cup surface 20 is properly positioned on the lens, the finger pressure on the suction bulb 16 is relaxed creating suction at the cup surface 20 wherein the lens is adhered thereto. Next, the person holds their eyelids wide open with the fingers of one hand and places the contact lens attached to cup surface 20 gently against the cornea of their eye and then slightly squeezes the suction bulb 16 using the thumb and index finger of their other hand gently pulling the cylindrical tube 12 away from the eyelid wherein the contact lens is released and positioned in the eye of the person for normal wear.

For removing a contact lens, the opposite procedure is applied wherein a person once again using their fingers slightly squeezes the suction bulb 16 while holding their eyelids wide open with the fingers of their other hand and places the cup surface 20 gently against the contact lens of their eye wherein the finger pressure on the suction bulb 16 is relaxed creating suction at the cup surface 20 wherein the contact lens is adhered thereto. The contact lens is now removed from the cornea by gently pulling it off by moving the cylindrical tube 12 away from the eyelid.

In one preferred embodiment, the cylindrical tube 12 of the contact lens applicator 10 is fabricated using a silicon material or the like having a straight portion 13 which is five inches long ending in the curved portion 14 being three inches long. Also, the center hole 22 may be ten millimeters in diameter with the outer holes 24 being 50% or less in diameter and the suction bulb 16 being 1" long in length 15 having a 1" diameter (1"×1") wherein the suction bulb 16 operates as a suction cup that functions as a trigger to push in and push out air to apply and release the contact lenses.

In summary, the present invention provides a contact lens applicator for soft contact lens which permits placement and release of the contact lens to the eye surface immediately upon contact with the eye through the use of a cup supporting surface whereby the soft lens can be shaped to the contour of the anterior surface of the cornea or sclera without damage to lens or eye in order to express most of the air bubbles from beneath the lens thereby significantly reducing the chance of the lens wrinkling or disengaging the eye on blinking. Additionally, the present invention allows the individual of not tilting his/her head backwards, placing a convenient solution to look straight while applying lenses.

Although the invention has been explained in relation to its preferred embodiment, it is to be understood that many other possible modifications and variations can be made without departing from the spirit and scope of the invention.

What is claimed is:

1. A contact lens removing apparatus, consisting essentially of:
   a. the elongated tube, having a first and second end;
   b. the flexible air bulb, coupled to a first end of the elongated tube, designed to be squeezed to blow air through the elongated tube, and released to suck air through the tube;
   c. a concave surface, located on the second end of the elongated tube, having a central hole therein, and a plurality of smaller periphery holes positioned around the central hole;
   d. wherein the elongated tube is bent by a certain angular amount at a certain distance between the first and second end thereof;
   e. wherein the central hole is at least 50% larger than the plurality of smaller periphery holes;
   f. wherein the periphery holes are at least 50% smaller than the central hole, and
   g. wherein the concave surface only has a single ring of smaller periphery holes equally distant from the central hole.

* * * * *